US008912236B2

(12) United States Patent
Kabra et al.

(10) Patent No.: US 8,912,236 B2
(45) Date of Patent: *Dec. 16, 2014

(54) PHARMACEUTICAL COMPOSITION FOR DELIVERY OF RECEPTOR TYROSINE KINASE INHIBITING (RTKI) COMPOUNDS TO THE EYE

(75) Inventors: Bhagwati P. Kabra, Euless, TX (US); Malay Ghosh, Fort Worth, TX (US); Adrian Sauceda, Keller, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/716,624

(22) Filed: Mar. 3, 2010

(65) Prior Publication Data

US 2010/0227904 A1  Sep. 9, 2010

Related U.S. Application Data

(60) Provisional application No. 61/156,919, filed on Mar. 3, 2009.

(51) Int. Cl.
| *A61K 47/30* | (2006.01) |
| *A61K 31/00* | (2006.01) |
| *A61K 31/416* | (2006.01) |
| *A61K 9/00* | (2006.01) |
| *A61K 47/34* | (2006.01) |

(52) U.S. Cl.
CPC ............. *A61K 31/416* (2013.01); *A61K 9/0051* (2013.01); *A61K 47/34* (2013.01); *Y10S 514/912* (2013.01)
USPC ............................. 514/772.7; 514/1; 514/912

(58) Field of Classification Search
USPC .......................................... 514/1, 912, 772.7
See application file for complete search history.

(56) References Cited

U.S. PATENT DOCUMENTS

| 3,856,919 | A | 12/1974 | Rankin |
| 3,931,319 | A | 1/1976 | Green et al. |
| 4,027,020 | A | 5/1977 | Green et al. |
| 4,407,791 | A | 10/1983 | Stark |
| 4,409,205 | A | 10/1983 | Shively |
| 4,525,346 | A | 6/1985 | Stark |
| 4,727,064 | A | 2/1988 | Pitha |
| 4,836,986 | A | 6/1989 | Ogunbiyi et al. |
| 4,983,586 | A | 1/1991 | Bodor |
| 5,024,998 | A | 6/1991 | Bodor |
| 5,037,647 | A | 8/1991 | Chowhan et al. |
| 5,300,287 | A | 4/1994 | Park |
| 5,461,081 | A | 10/1995 | Ali et al. |
| 5,624,962 | A | 4/1997 | Takeuchi et al. |
| 5,756,552 | A | 5/1998 | Takeuchi et al. |
| 5,767,079 | A * | 6/1998 | Glaser et al. ................. 424/427 |
| 5,932,572 | A | 8/1999 | Dean et al. |
| 6,139,794 | A | 10/2000 | Asgharian et al. |
| 6,232,343 | B1 | 5/2001 | Ikari et al. |
| 6,284,804 | B1 | 9/2001 | Singh et al. |
| 6,359,016 | B2 | 3/2002 | Singh et al. |
| 6,624,193 | B1 | 9/2003 | Naka et al. |
| 6,743,439 | B1 | 6/2004 | Castillo et al. |
| 7,001,615 | B1 | 2/2006 | Singh et al. |
| 2002/0037877 | A1 | 3/2002 | Singh |
| 2003/0139382 | A1 | 7/2003 | Wall et al. |
| 2003/0165568 | A1 | 9/2003 | Colombo et al. |
| 2004/0235892 | A1 | 11/2004 | Dai et al. |
| 2004/0256749 | A1 | 12/2004 | Chaubal et al. |
| 2005/0245497 | A1 | 11/2005 | Penfold et al. |
| 2006/0024374 | A1 | 2/2006 | Gasco et al. |
| 2006/0122277 | A1 | 6/2006 | Wong |
| 2006/0134198 | A1 | 6/2006 | Tawa et al. |
| 2006/0172969 | A1 | 8/2006 | Suzuki et al. |
| 2006/0189608 | A1 | 8/2006 | Bingaman |
| 2006/0257486 | A1 | 11/2006 | Owen et al. |
| 2006/0257487 | A1 | 11/2006 | Owen et al. |
| 2007/0060887 | A1 * | 3/2007 | Marsh et al. .................. 604/113 |
| 2007/0149593 | A1 | 6/2007 | Ghosh et al. |
| 2007/0173538 | A1 * | 7/2007 | Han et al. ...................... 514/406 |
| 2007/0249546 | A1 | 10/2007 | Sawaya |
| 2008/0112895 | A1 * | 5/2008 | Kottayil et al. ................. 424/46 |
| 2008/0299206 | A1 * | 12/2008 | Lee et al. ...................... 424/489 |

FOREIGN PATENT DOCUMENTS

| JP | 5155767 | 6/1993 |
| JP | 5186351 | 7/1993 |
| JP | 10287552 | 10/1998 |
| JP | 2000513001 | 10/2000 |
| JP | 2007500226 | 1/2007 |
| JP | 2008531593 | 8/2008 |
| JP | 2008540533 | 11/2008 |
| WO | 9109523 | 7/1991 |
| WO | 2006121964 A2 | 11/2006 |
| WO | 2007076358 A1 | 7/2007 |

(Continued)

OTHER PUBLICATIONS

ChemBuyersGuide.com, Chemax Performance Products, Feb. 7, 2005, printed from http://web.archive.org/web/20050207180816/http://www.chembuyersguide.com/partners/chemax.html, 18 pages.*
Rowe, Handbook of Pharmaceutical Excipients-Polyethylene Glycol, Pharmaceutical Press, 2003, 454-459.*
Albers, E., et al., "Cyclodextrin Derivatives in Pharmaceutics," Critical Reviews in Therapeutic Drug Carrier Systems, 1995, pp. 311-337, vol. 12(4).
Loftsson, Thorsteinn, et al., "Pharmaceutical Applications of Cyclodextrins. 1. Drug Solubilization and Stabilization," J. Pharm. Sci., 1996, pp. 1017-1025, vol. 859(10).
Loftsson, Thorsteinn, et al., "Cyclodextrins in Ophthalmic Drug Delivery," Advanced Drug Delivery Reviews, 1999, pp. 59-79, vol. 36.

(Continued)

*Primary Examiner* — Gigi Huang
(74) *Attorney, Agent, or Firm* — Scott A. Chapple

(57) ABSTRACT

The present invention relates to development of efficacious pharmaceutical implant compositions comprising an active agent in a therapeutically effective amount and a polyethylene glycol having a molecular weight of at least 2000.

7 Claims, No Drawings

(56) References Cited

FOREIGN PATENT DOCUMENTS

| WO | 2007076448 A2 | 7/2007 |
|---|---|---|
| WO | 2008076819 A2 | 6/2008 |
| WO | 2009014510 A1 | 1/2009 |
| WO | 2010065730 | 6/2010 |
| WO | 2010101971 A1 | 9/2010 |

OTHER PUBLICATIONS

Loftsson, Thorsteinn, et al., "Cyclodextrins in Eye Drop Formulations: Enhanced Topical Delivery of Corticosteroids to the Eye," Acta Ophthalmologica Scandinavica, 2002, pp. 144-150, vol. 80.

Menard, F. A., et al., "Physico-Chemical Aspects of the Complexaion of Some Drugs with Cyclodextrins," Drug Development and Industrial Pharmacy, Jan. 1990, pp. 91-113, vol. 16(1).

Challa, et al., "Cyclodextrins in Drug Delivery: An Updated Review," AAPS PharmSciTech, 2005, pp. E329-E357, vol. 6(2).

Rajewski, Roger A., et al., "Pharmaceutical Applications of Cyclodextrins. 2. In Vivo Drug Delivery," Journal of Pharmaceutical Sciences, 1996, pp. 1142-1169, vol. 85(11).

Szejtli, J., "Medicinal Applications of Cyclodextrins," Medicinal Research Reviews, 1994, pp. 353-386, vol. 14(3).

Szejtli, J., "Introduction and General Overview of Cyclodextrin Chemistry," Chem. Rev. 1998, pp. 1743-1753, vol. 98.

Uekama, Kaneto, et al., "Cyclodextrin Drug Carrier Systems," Chem. Rev. 1998, pp. 2045-2076, vol. 98.

Derwent and Mieler; "Thermoresponsive hydrogels as a new ocular drug delivery platform to the posterior segment of the eye"; Trans Am. Ophthalmol. Soc.; vol. 106; pp. 206-214 (2008).

Datta; "Characterization of polyethylene glycol hydrogels for biomedical applications"; A Thesis; Louisiana State University; Department of Chemical Engineering; pp. 1-107; 2007.

International Pharmaceutical Excipients Council Japan, Pharmaceutical Excipients Directory, 1994, pp. 128-129.

PCT International Preliminary Report on Patentability for PCT/US2009/066570 with mailing date Jun. 16, 2011.

PCT International Search Report for corresponding PCT/US2009/066570 with mailing date Feb. 25, 2011.

PCT International Written Opinion for corresponding PCT/US2009/066570 with mailing date Feb. 25, 2011.

\* cited by examiner

PHARMACEUTICAL COMPOSITION FOR DELIVERY OF RECEPTOR TYROSINE KINASE INHIBITING (RTKI) COMPOUNDS TO THE EYE

This application claims priority under 35 U.S.C. §119 to U.S. Provisional Patent Application No. 61/156,919 filed Mar. 3, 2009, the entire contents of which are incorporated herein by reference.

BACKGROUND OF THE INVENTION

1. Field of the Invention

The present invention relates to unique compositions containing compounds with poor solubility and methods useful for treating pathological states that arise or are exacerbated by ocular angiogenesis, inflammation and vascular leakage such as AMD, DR, diabetic macular edema etc., and more specifically, to compositions containing agent with anti-angiogenic, anti-inflammatory or anti-vascular permeability property for use in treating ocular disorders.

2. Description of the Related Art

Abnormal neovascularization or angiogenesis and enhanced vascular permeability are major causes for many ocular disorders including age-related macular degeneration (AMD), retinopathy of prematurity (ROP), ischemic retinal vein occlusions and diabetic retinopathy (DR). AMD and DR are among the most common cause of severe, irreversible vision loss. In these and related diseases, such as retinal vein occlusion, central vision loss is secondary to angiogenesis, the development of new blood vessels from pre-existing vasculature, and alterations in vascular permeability properties.

The angiogenic process is known by the activation of quiescent endothelial cells in pre-existing blood vessels. The normal retinal circulation is resistant to neovascular stimuli, and very little endothelial cell proliferation takes place in the retinal vessels. While there appear to be many stimuli for retinal neovascularization, including tissue hypoxia, inflammatory cell infiltration and penetration barrier breakdown, all increase the local concentration of cytokines (VEGF, PDGF, FGF, TNF, IGF etc.), integrins and proteinases resulting in the formation of new vessels, which then disrupt the organizational structure of the neural retina or break through the inner limiting membranes into the vitreous. Elevated cytokine levels can also disrupt endothelial cell tight junctions, leading to an increase in vascular leakage and retinal edema, and disruption of the organizational structure of the neural retina. Although VEGF is considered to be a major mediator of inflammatory cell infiltration, endothelial cell proliferation and vascular leakage, other growth factors, such as PDGF, FGF, TNF, and IGF etc., are involved in these processes. Therefore, growth factor inhibitors can play a significant role in inhibiting retinal damage and the associated loss of vision upon local delivery in the eye or via oral dosing.

There is no cure for the diseases caused by ocular neovascularization and enhanced vascular permeability. The current treatment procedures of AMD include laser photocoagulation and photodynamic theraphy (PDT). The effects of photocoagulation on ocular neovascularization and increased vascular permeability are achieved only through the thermal destruction of retinal cells. PDT usually requires a slow infusion of the dye, followed by application of non-thermal laserlight. Treatment usually causes the abnormal vessels to temporarily stop or decrease their leaking PDT treatment may have to be repeated every three months up to 3 to 4 times during the first year. Potential problems associated with PDT treatment include headaches, blurring, and decreased sharpness and gaps in vision and, in 1-4% of patients, a substantial decrease in vision with partial recovery in many patients. Moreover, immediately following PDT treatment, patients must avoid direct sunlight for 5 days to avoid sunburn. Recently, a recombinant humanized IgG monoclonal antibody fragment (ranibizumab) was approved in the US for treatment of patients with age-related macular degeneration. This drug is typically administered via intravitreal injection once a month.

Many compounds that may be considered potentially useful in treating ocular neovascularization and enhanced vascular permeability-related and other disorders, are poorly soluble in water. A poorly water soluble compound is a substance that is not soluble at a therapeutically effective concentration in an aqueous physiologically acceptable vehicle. Aqueous solubility is an important parameter in formulation development of a poorly water soluble compound. What is needed is a formulation that provides increased solubility of the compound while also providing sufficient bioavailability of the compound so as to maintain its therapeutic potential.

The present invention provides safe and effective formulations for ocular administration of poorly soluble compounds for the treatment of ocular diseases caused by endothelial cell proliferation, vascular leakage, inflammation and angiogenesis.

SUMMARY OF THE INVENTION

The present invention overcomes these and other drawbacks of the prior art by providing compositions for treating ocular diseases due to angiogenesis, enhanced endothelial cell proliferation, inflammation, or increased vascular permeability. Within one aspect of the present invention, a pharmaceutical composition is provided wherein an active agent is incorporated into polyethylene glycol (PEG) having a molecular weight of is greater than 2000 to develop an intraocular implant for sustained delivery of the compound for use in vitreoretinal therapy, in treating angiogenesis-related ocular disorders, inhibiting neovascularization, controlling vascular permeability, treating inflammation, and improving vision. The bioavailability of the compounds for use in the compositions of the present invention is substantially enhanced via use of a higher molecular weight PEG (e.g., MW≥2000) into the composition. The compositions of the invention will be solid, or waxy, at room temperature and will liquefy upon heating. For delivery, the composition of the invention will be heated in order to liquefy it and it will form the waxy solid upon injection into the eye of a patient. The solid form of the composition allows for sustained delivery of the active compound to the tissues at the back of the eye, thereby treating angiogenesis-related ocular disorders, inhibiting neovascularization, controlling vascular permeability, treating inflammation, and/or improving vision.

The composition can also comprise an active agent in an amount of from 0.01% to 20%, and a polyethylene glycol having a molecular weight of at least 2000 in an amount from 40% to 98%, wherein said composition (a) is a solid at body temperature; (b) is capable of injection into the eye of a patient upon heating said composition to its melting point; and (c) solidifies upon injection into the eye of a patient.

The concentration of the anti-angiogenic, anti-inflammatory, or anti-vascular permeability agent used in this present invention varies depending on the ophthalmic diseases and the route of administration used, and any concentration may be employed as long as its effect is exhibited. Thus, although the concentration is not restricted, a concentration of 0.001% to 25 wt % is preferred. The concentration of PEG will vary depending on the concentration of active used in the formulation. Although the concentrations are not restricted, usually, the preferred concentration of the PEG in the intravitreal composition is from 30% to 99.9%, more preferred concentration is 50% to 99% and most preferred concentration is 70% to 98%.

A wide variety of molecules may be utilized within the scope of present invention. For examples molecules having poor solubility; biologic molecules, such as antibodies, fragments thereof (including scFvs, Fab fragments,), polypeptides, siRNA molecules; or any active agent for which sustained release into ocular tissues is desirable. As used herein, the term "poor solubility" is used to refer to a compound having solubility in water or vehicle of less than 500 µg/mL, well below its therapeutic window.

The compositions of the present invention are preferably administered to the eye of a patient suffering from an angiogenesis or enhanced vascular permeability related ocular disorder, or a disorder characterized by neovascularization or vascular permeability, or a geographic atrophy disorder or macular edema, via posterior juxtascleral administration, intravitreal injection, or vitreoretinal therapy.

DETAILED DESCRIPTION PREFERRED EMBODIMENTS

As noted above, the present invention provides compositions that contain an active agent having poor water solubility, for use in the treatment of ocular disorders caused by endothelial cell proliferation, enhanced vascular permeability, inflammation, or angiogenesis. The compositions of the invention are useful in treating disorders associated with microvascular pathology, increased vascular permeability and intraocular neovascularization, including diabetic retinopathy (DR), age-related macular degeneration (AMD), geographic atrophy, uveitis, and retinal or macular edema.

Briefly, within the context of the present invention, an active agent should be understood to be any molecule, either synthetic or naturally occurring, which acts to inhibit vascular growth, reduce vascular permeability, and/or decrease inflammation. In particular, the present invention provides compositions comprising an insoluble, or poorly soluble, active agent in a therapeutically effective amount solubilized into high molecular weight PEG (i.e., MW≥2000) for ophthalmic use. As used herein, when referring to a PEG of a particular molecular weight, the term "PEG" will be followed by a number, indicating the molecular weight for that particular PEG. For example, PEG 400 refers to a PEG having a molecular weight of approximately 400. Of course, the skilled artisan will understand that a designation of PEG 400 will refer to a range of PEGs having molecular weights of about 400 and will encompass PEGs with molecular weights above or below 400 by anywhere from 1-50%

Polyethylene glycols (PEGs) are widely used in a variety of pharmaceutical formulations including parenteral, topical, ophthalmic, oral and rectal preparations. PEGs are stable, hydrophilic substances and are non-irritating to the skin.

Although PEGs have been used in ophthalmic preparations, they have not been used as the main vehicle of a solid implant for intraocular use. They have typically been used as an excipient to modify the properties of implants based on other materials, such as a lipid or a biodegradable polymer. They have also been used as an excipient in liquid formulations, e.g., PEG 400 has been used as an excipient in aqueous intravitreal suspension formulations.

The present invention is based, in part, upon the discovery that formulations incorporating PEGs with higher molecular weights (i.e., MW≥2000) as the main vehicle provides a solid implant for intraocular use. The melting points of PEG is a function of its molecular weight. For example, the melting point ranges for PEG 1000, PEG 2000, PEG 4000, and PEG 8000 are 37 to 40° C., 45 to 50° C., 50 to 58° C., and 60 to 63° C., respectively.

Incorporating a PEG having a melting point that is substantially higher than the human intraocular temperature of about 37° C. into an ophthalmic formulation as the main vehicle provides a composition that can be heated to its melting point and injected into the eye as a liquid. Upon entry into the eye, the composition will cool to the intraocular temperature of about 37° C. By virtue of its hydrophilic nature, the PEG will solidify, thus providing sustained delivery of the active agent to the retinal tissues. Moreover, PEG is a good solvent and can provide the added benefit of solubilizing the active agents incorporated into the composition causing the release of active agent to be higher than that typically obtained using lipid based implants.

The density of PEG is about 1.08, much higher than the density of implants based upon lipids (e.g., <1). Thus, an implant based upon a PEG vehicle may sink to the bottom of the vitreous when injected into the eye, whereas a lipid-based implant may remain at the site of injection or float within the vitreous.

It is contemplated that any active agent that is poorly water soluble, or slighlty to soluble, may be included in the compositions of the present invention. In other instances, highly water soluble active agents may also be included in the compositions of the present invention. In another instance, biologics will be useful in the compositions of the invention. The term "biologic" as used herein includes, but is not limited to, proteins (including peptides, polypeptides, and antibodies, for example), sugars (including carbohydrates, for example), nucleic acids (including oligonucleotides and polynucleotides, for example), cells, tissues, and combinations thereof. As used herein, the terms "antibody" or "antibodies" include a whole antibody (including polyclonal and monoclonal antibodies) and antibody fragments containing antigen-binding portions thereof. The term "antibody" includes any monospecific or bispecific compound comprised of a sufficient portion of a light chain variable region and/or a heavy chain variable region to effect binding to an epitope to which the whole antibody has binding specificity. The fragments can include the variable region of at least one heavy or light chain immunoglobulin polypeptide, and include, but are not limited to, Fab, Fab', F(ab')2, Fv, and single-chain antibodies. Binding fragments are typically produced by recombinant DNA techniques, or by enzymatic or chemical cleavage of intact antibodies.

For example, it is contemplated that anti-angiogenic agents, anti-inflammatory agents, or anti-vascular permeability agents are useful in the compositions of the invention. Preferred anti-angiogenic agents include, but are not limited to, receptor tyrosine kinase inhibitors (RTKi), in particular, those having a multi-targeted receptor profile such as that described in further detail herein; angiostatic cortisenes; MMP inhibitors; integrin inhibitors; PDGF antagonists; antiproliferatives; HIF-1 inhibitors; fibroblast growth factor inhibitors; epidermal growth factor inhibitors; TIMP inhibitors; insulin-like growth factor inhibitors; TNF inhibitors; antisense oligonucleotides; etc. and prodrugs of any of the aforementioned agents. The preferred anti-angiogenic agent for use in the present invention is a multi-targeted receptor tyrosine kinase inhibitor (RTKi). Most preferred are RTKi's with multi-target binding profiles, such as N-[4-(3-amino-1H-indazol-4-yl) phenyl]-N'-(2-fluoro-5-methylphenyl)

urea, having the binding profile substantially similar to that listed in Table 1. Additional multi-targeted receptor tyrosine kinase inhibitors contemplated for use in the compositions of the present invention are described in U.S. Application Serial No. 2004/0235892, incorporated herein by reference. As used herein, the term "multi-targeted receptor tyrosine kinase inhibitor" refers to a compound having a receptor binding profile exhibiting selectivity for multiple receptors shown to be important in angiogenesis, such as the profile shown in Table 1, and described in co-pending U.S. application serial number 2006/0189608, incorporated herein by reference. More specifically, the preferred binding profile for the multi-targeted receptor tyrosine kinase inhibitor compounds for use in the compositions of the present invention is KDR (VEGFR2), Tie-2 and PDGFR.

TABLE 1

Kinase Selectivity Profile of a RTK Inhibitor

| KDR | FLT1 | FLT4 | PDGFR | CSF1R | KIT | FLT3 | TIE2 | FGFR | EGFR | SRC |
|---|---|---|---|---|---|---|---|---|---|---|
| 4 | 3 | 190 | 66 | 3 | 14 | 4 | 170 | >12,500 | >50,000 | >50,000 |

All data reported as IC50 values for kinase inhibition in cell-free enzymatic assays;
ND denotes no data.
Values determined @ 1 mM ATP.

Other agents which will be useful in the compositions and methods of the invention include anti-VEGF antibody (i.e., bevacizumab or ranibizumab); VEGF trap; siRNA molecules, or a mixture thereof, targeting at least two of the tyrosine kinase receptors having $IC_{50}$ values of less than 200 nM in Table 1; glucocorticoids (i.e., dexamethasone, fluorometholone, medrysone, betamethasone, triamcinolone, triamcinolone acetonide, prednisone, prednisolone, hydrocortisone, rimexolone, and pharmaceutically acceptable salts thereof, prednicarbate, deflazacort, halomethasone, tixocortol, prednylidene (21-diethylaminoacetate), prednival, paramethasone, methylprednisolone, meprednisone, mazipredone, isoflupredone, halopredone acetate, halcinonide, formocortal, flurandrenolide, fluprednisolone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, and deacylcortivazol oxetanone); Naphthohydroquinone antibiotics (i.e., Rifamycin); and NSAIDs (i.e., nepafenac, amfenac).

It is contemplated that virtually any PEG with a molecular weight greater than 2000 can be used in the compositions and methods of the invention. Preferred PEGs for use in the compositions and methods of the invention include PEG 3000, PEG 4000, PEG 6000, PEG 8000 and PEG 20000. It is further contemplated that mixtures of higher molecular PEGs may be utilized in the compositions and methods of the invention.

The formulations of the present invention provide a number of advantages over conventional formulations. One advantage of the present invention is that PEGs can successfully solubilize poorly soluble compounds, allowing the preparation of an efficacious ophthalmologically acceptable intravitreal, PJ and/or periocular formulation for local ocular delivery. Additionally, bioavailability of the drug can be modulated by controlling the molecular weight of the PEG used in the formulation. Furthermore, the preparation can be injected using a 27 or 30 gauge needle. Toxicity of the active agent can be reduced or suitably modulated. Another advantage of the present invention is that stability of biologics may be improved in the PEG based solid dosage form described herein.

The present inventors have discovered that use of higher molecular weight PEGs to solubilize and deliver highly insoluble anti-angiogenic active compounds provides an efficacious ophthalmic formulation. For example, the compound N-[4-(3-amino-1H-indazol-4-yl) phenyl]-N'-(2-fluoro-5-methylphenyl) urea has extremely poor solubility in phosphate buffer, pH 7.2 (0.00059 mg/mL). Prototype intravitreal vehicle is shown in Example 1, and intravitreal and PJ formulations of the active compound containing PEG are provided in Examples 2 and 3, respectively.

In certain preferred embodiments, the formulation of the invention will further comprise a lipid to modulate the delivery of the drug and to extend the duration. Some examples of a lipid include triglycerides, diglycerides, monoglycerides, propylene glycol esters, PEF esters of fatty acid and their mixtures. Preferred lipids include glyceryl monolaurate; glyceryl dilaurate; glyceryl monomyristate; glyceryl dimyristate; glyceryl monopalmitate; glyceryl dipalmitate; glyceryl monostearate; glyceryl distearate; glyceryl monooleate; glyceryl dioleate; glyceryl monolinoleate; glyceryl dilinoleate; glyceryl monoarachidate; glyceryl diarachidate; glyceryl monobehenate; glyceryl dibehenate; diethylene glycol monostearate; propylene glycol monostearate; glyceryl monostearate; glyceryl monolinoleate; glyceryl monooleate; glyceryl monopalmitate; and mixtures thereof. A preferred example of the lipid is glyceryl palmitostearate. One commercial brand of glyceryl palmitostearate is PRECIROL®. The concentration of a lipid is generally less than 31 wt %, preferably less than 14% and most-preferably less than 8%

The specific dose level of the active agent for any particular human or animal depends upon a variety of factors, including the activity of the active compound used, the age, body weight, general health, time of administration, route of administration, and the severity of the pathologic condition undergoing therapy.

The formulations described herein may be delivered via intravitreal injection, via posterior juxtascleral, and periocular routes. In preferred embodiments of the present invention, the amount of active agent, or poorly water soluble agent, or biologic will be from about 0.001% to 30% for intravitreal administration. More preferably from 0.05% to 20% and most preferably from 0.1% to 18%.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

10% RTK inhibiting compound, 90% PEG 4000

13.5 g PEG 4000 was heated above 55° C. to melt it. 1.5 g of the compound N-[4-(3-amino-1H-indazol-4-yl) phenyl]-N'-(2-fluoro-5-methylphenyl) urea was added to it. The drug completely dissolved in PEG 4000. The melt was poured into a mold. Upon cooling, translucent, solid inserts (pellets or implants) of about 10 mg weight were obtained.

When the insert is placed in water in a 4 ml scintillation vial, it sinks to the bottom and swells slightly to form a gel and become white.

EXAMPLE 2

20% RTK inhibitor, 50% PEG 4000, 30% PRECIROL®

A mixture of 9 g PEG 4000, 3.6 g of the RTKi (N-[4-(3-amino-1H-indazol-4-yl) phenyl]-N'-(2-fluoro-5-methylphenyl) urea), and 6 g PRECIROL® were heated to melt PEG 4000 and PRECIROL®. A major portion of the RTKi was dissolved. The melt was poured into the mold. Upon cooling, whitish solid inserts (pellets or implants) of about 10 mg weight were obtained.

EXAMPLE 3

18% RTK inhibiting compound, 82% PEG 4000

9 g of PEG 4000 was heated above 55° C. to melt it. 2 g of the RTKi (N-[4-(3-amino-1H-indazol-4-yl) phenyl]-N'-(2-fluoro-5-methylphenyl) urea) was added to it. The RTKi compound completely dissolved in the PEG 4000. The melt was poured into the mold. Upon cooling, translucent solid inserts (pellets or implants) of about 10 mg weight were obtained.

EXAMPLES 4 TO 5

The PEG based compositions of examples 4 and 5 are given bleow.

| Ingredients | Examples 4 w/w % | 5 w/w % |
|---|---|---|
| RTKi compound | 18 | 12 |
| Polyethylene glycol 6000 | — | 44 |
| Polyethylene glycol 20000 | — | 44 |
| Polyethylene glycol 14000 | 72 | — |

A pharmacokinetic study was performed in FIX rabbits by giving a 9 mg injection of the composition of examples 4 and 5 by heating them above 60° C. to inferotemporal quadrant of the vitreous. The levels of RTKi observed in the central retina were determined by LC/MS/MS analysis. These levels are provided below.

| Examples | 4 | 5 |
|---|---|---|
| Weight (mg) | 9 | 18 |
| Dose (µg) | 1600 | 2160 |
| RTKi concentration (µM) in Retina at Day 2, | 60.0 | 50.2 |
| RTKi concentration (µM) in Retina at Day 14, | 19.9 | 12.7 |
| RTKi concentration (µM) in Retina at Day 28, | 3.0 | NT |
| RTKi concentration (µM) in Retina at Day 56, | NT | 4.6 |

EXAMPLES 6 to 8

The PEG based compositions with PRECIROL of examples 6 through 8 are given below.

| Ingredients | Examples 6 w/w % | 7 w/w % | 8 w/w % |
|---|---|---|---|
| RTKi | 12 | 12 | 12 |
| Glyceryl palimitostearate (PRECIROL ®) | 3 | 7.5 | 15 |
| Polyethylene glycol 6000 | 85 | 85 | 73 |

A pharmacokinetic study was performed in F1X rabbits by giving a 9 mg injection of the composition of examples 6 through 8 by heating them above 60° C. to inferotemporal quadrant of the vitreous. The levels of RTKi observed in the central retina were determined by LC/MS/MS analysis. These levels are provided below.

| Examples | 6 | 7 | 8 |
|---|---|---|---|
| Weight (mg) | 9 | 9 | 9 |
| Dose (µg) | 1080 | 1080 | 1080 |
| RTKi concentration (µM) in Retina at Day 2, | 10.4 | 5.3 | NT |
| RTKi concentration (µM) in Retina at Day 14, | 3.2 | 1.1 | 3.3 |
| RTKi concentration (µM) in Retina at Day 28, | NT | NT | 2.1 |
| RTKi concentration (µM) in Retina at Day 56, | 1.4 | NT | NT |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both to chemically and structurally related may be substituted for the agents described herein to achieve similar results. All such substitutions and modifications apparent to those skilled in the art are deemed to be within the spirit, scope and concept of the invention as defined by the appended claims.

References

All references cited herein, to the extent that they provide exemplary procedural or other details supplementary to those set forth herein, are specifically incorporated herein by reference.

We claim:

1. A method for treating age-related macular degeneration in a patient in need thereof with a therapeautically effective amount of a multi-targeted receptor tyrosine kinase inhibitor comprising:

heating an ophthalmic composition to its melting point to liquefy the ophthalmic composition, the ophthalmic composition comprising the multi-targeted receptor tyrosine kinase inhibitor in an amount of from 0.01% to 20% and polyethylene glycol having a molecular weight of at least 6000 in an amount from 40% to 98%;

injecting into an eye of the patient the ophthalmic composition in liquid form after heating; and allowing the composition to cool in the eye of the patient causing the composition to solidify in the eye of the patient.

2. The method of claim 1, wherein the composition comprises:

18% (w/w) multi-targeted receptor tyrosine kinase inhibitor; and

72% (w/w) PEG14000.

3. The method of claim 1, wherein the composition comprises:

12% (w/w) multi-targeted receptor tyrosine kinase inhibitor;

44% (w/w) PEG6000; and

44% (w/w) PEG20000.

4. The method of claim 1, wherein the composition comprises:

12% (w/w) multi-targeted receptor tyrosine kinase inhibitor;

3% (w/w) glycerol palmitostearate; and

85% (w/w) PEG6000.

5. The method of claim 1, wherein the composition comprises:

12% (w/w) multi-targeted receptor tyrosine kinase inhibitor;

15% (w/w) glycerol palmitostearate; and

73% (w/w) PEG6000.

6. The method of claim 1, wherein the PEG is selected from the group consisting of PEG6000, PEG20000, and a mixture of PEG6000 and PEG20000.

7. The method of claim 1, wherein the preparation is injected using a 27 or 30 gauge needle.

* * * * *